United States Patent
Morita

(10) Patent No.: US 11,170,541 B2
(45) Date of Patent: Nov. 9, 2021

(54) DEPTH MAP CREATION APPARATUS THAT CREATES A PLURALITY OF DEPTH MAPS ON THE BASIS OF A PLURALITY OF SPATIAL FREQUENCY COMPONENTS AND PLURALITY OF TOMOGRAPHIC IMAGES

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 78 days.

(21) Appl. No.: 16/661,998

(22) Filed: Oct. 23, 2019

(65) Prior Publication Data

US 2020/0134884 A1 Apr. 30, 2020

(30) Foreign Application Priority Data

Oct. 29, 2018 (JP) .............................. JP2018-202947

(51) Int. Cl.
| | | |
|---|---|---|
| *G06T 11/00* | (2006.01) | |
| *G06T 7/55* | (2017.01) | |
| *A61B 6/02* | (2006.01) | |
| *A61B 6/00* | (2006.01) | |
| *G06T 7/00* | (2017.01) | |

(52) U.S. Cl.
CPC ............ *G06T 11/003* (2013.01); *A61B 6/025* (2013.01); *A61B 6/502* (2013.01); *G06T 7/0012* (2013.01); *G06T 7/55* (2017.01); *G06T 2207/30068* (2013.01)

(58) Field of Classification Search
CPC ....... G06T 11/003; G06T 7/55; G06T 7/0012; G06T 2207/30068; G06T 2211/436; G06T 11/008; G06T 7/30; G06T 2207/10028; A61B 6/025; A61B 6/502; A61B 6/5235; A61B 6/469; A61B 6/032; A61B 6/461
See application file for complete search history.

(56) References Cited

U.S. PATENT DOCUMENTS

| | | | |
|---|---|---|---|
| 2009/0080765 A1 | 3/2009 | Bernard et al. | |
| 2015/0302615 A1* | 10/2015 | Fukuda ................. | G06T 11/006 378/19 |
| 2016/0095563 A1 | 4/2016 | Fukuda et al. | |
| 2016/0206268 A1 | 7/2016 | Fukuda | |

FOREIGN PATENT DOCUMENTS

| | | |
|---|---|---|
| KR | 20160086802 A | 7/2016 |
| WO | 2014/203531 A1 | 12/2014 |

OTHER PUBLICATIONS

Extended European Search Report dated Dec. 13, 2019, issued in corresponding EP Patent Application No. 19205403.9.

* cited by examiner

*Primary Examiner* — Siamak Harandi
(74) *Attorney, Agent, or Firm* — Solaris Intellectual Property Group, PLLC

(57) ABSTRACT

An image display apparatus includes a depth map creating unit that creates, on the basis of a two-dimensional radiation image and a plurality of tomographic images for the same subject, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information.

11 Claims, 9 Drawing Sheets

FIG. 6
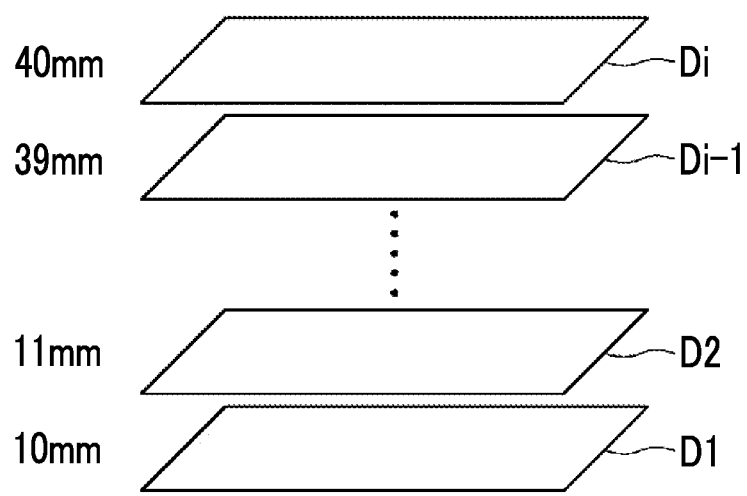
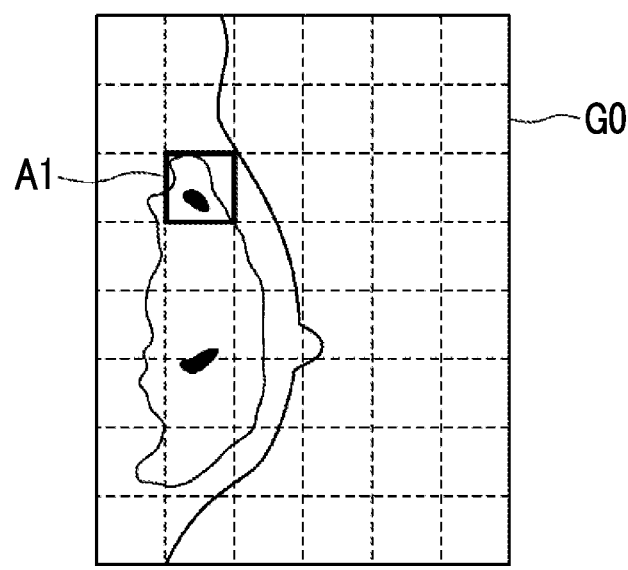

| 10 | 10 | 10 | 10 | 10 | 10 | 10 | 10 |
|----|----|----|----|----|----|----|----|
| 10 | 10 | 10 | 10 | 10 | 10 | 10 | 10 |
| 21 | 20 | 39 | 18 | 23 | 35 | 31 | 15 |
| 32 | 28 | 23 | 28 | 26 | 15 | 12 | 29 |
| 31 | 16 | 20 | 24 | 16 | 18 | 23 | 17 |
| 30 | 15 | 14 | 37 | 15 | 14 | 28 | 31 |

MP2

| 10 | 10 | 10 | 10 | 10 | 10 | 10 | 10 |
|----|----|----|----|----|----|----|----|
| 10 | 10 | 10 | 10 | 10 | 10 | 10 | 10 |
| 18 | 39 | 22 | 37 | 15 | 14 | 26 | 30 |
| 39 | 18 | 23 | 28 | 31 | 27 | 28 | 38 |
| 12 | 29 | 25 | 22 | 18 | 17 | 16 | 23 |
| 22 | 18 | 23 | 14 | 16 | 30 | 35 | 33 |

MP1

| 10 | 10 | 10 | 10 | 10 | 10 | 10 | 10 |
|----|----|----|----|----|----|----|----|
| 10 | 10 | 10 | 10 | 10 | 10 | 10 | 10 |
| 21 | 23 | 20 | 20 | 24 | 23 | 22 | 21 |
| 31 | 22 | 27 | 26 | 23 | 10 | 18 | 32 |
| 40 | 31 | 30 | 24 | 16 | 12 | 26 | 31 |
| 26 | 15 | 10 | 15 | 13 | 23 | 25 | 30 |

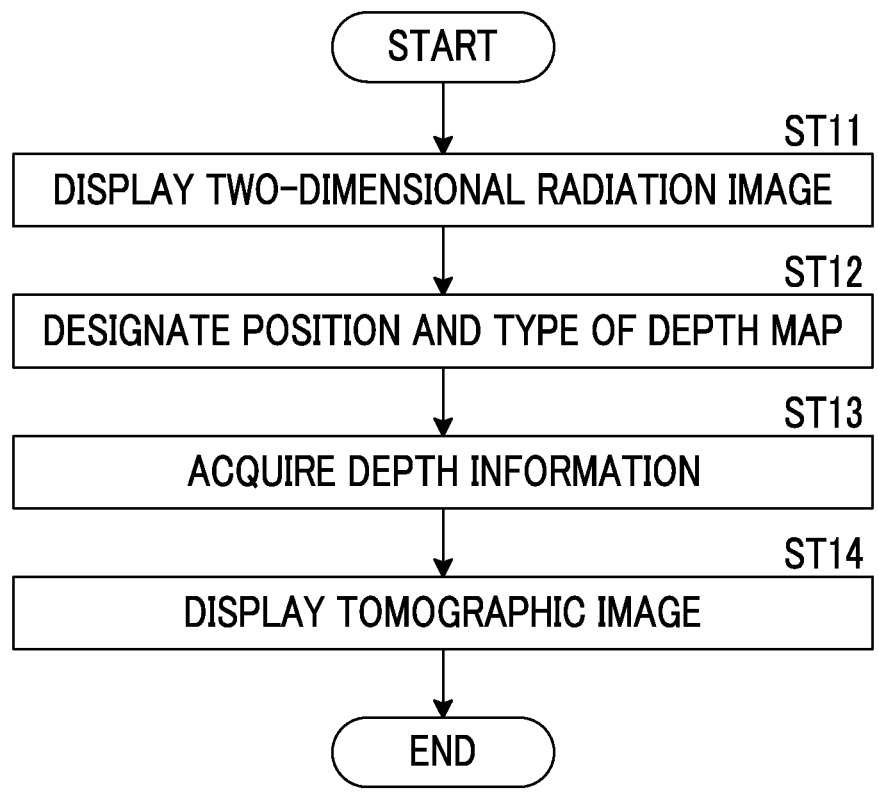
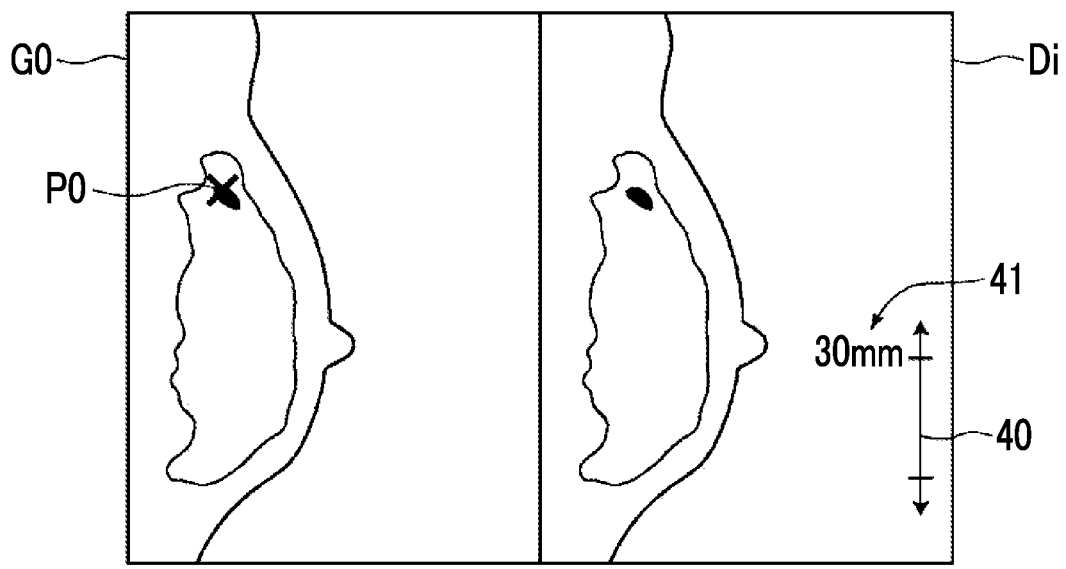

DEPTH MAP CREATION APPARATUS THAT CREATES A PLURALITY OF DEPTH MAPS ON THE BASIS OF A PLURALITY OF SPATIAL FREQUENCY COMPONENTS AND PLURALITY OF TOMOGRAPHIC IMAGES

CROSS REFERENCE TO RELATED APPLICATIONS

The present application claims priority under 35 U.S.C. § 119 to Japanese Patent Application No. 2018-202947 filed on Oct. 29, 2018. The above application is hereby expressly incorporated by reference, in its entirety, into the present application.

BACKGROUND OF THE INVENTION

1. Field of the Invention

The present disclosure relates to an image display apparatus, a radiation imaging display system, an image display method, and an image display program.

2. Description of the Related Art

In displaying a medical image such as a radiation image to perform image diagnosis, a technique for performing cross reference between a two-dimensional radiation image acquired by plain radiography and tomographic images acquired through tomography using a computed tomography (CT) apparatus, a magnetic resonance imaging (MRI) apparatus, a tomosynthesis imaging apparatus, or the like has been used. For example, in order to perform image diagnosis of a breast, a technique for confirming of the presence or absence of a lesion (tumor or calcification) in the breast by perform cross reference between two-dimensional radiation images acquired by performing plain radiography in a variety of imaging directions, such as a craniocaudal (CC) imaging for performing imaging by irradiating radiation from an upper side, mediolateral (ML) imaging for performing imaging by irradiating radiation from a lateral side, a mediolateral oblique (MLO) imaging for performing imaging by irradiating radiation in an oblique direction, or the like, and tomographic images generated by reconstructing a plurality of radiation images acquired through tomosynthesis imaging in the variety of imaging directions has been used.

The tomosynthesis imaging is a method for performing imaging by irradiating radiation to a subject in a plurality of different directions while moving a radiation source and reconstructing an image acquired in this way to obtain an image in which a desired cross-section is emphasized. In the tomosynthesis imaging, in accordance with characteristics of an imaging apparatus and necessary tomographic images, a plurality of radiation images are acquired by imaging the subject at a plurality of irradiation positions having different irradiation angles by moving the radiation source in parallel with a radiation detector or moving the radiation source to draw an arc of a circle or an ellipse, and tomographic images are generated by reconstructing these radiation images using a back-projection method such as a simple back-projection method or a filtered back-projection method.

Here, a two-dimensional radiation image has merits in that perspicuity is excellent, sharpness is high, and it is easy to compare the two-dimensional radiation image with a previous image, as compared with a tomographic image. Accordingly, cross reference between the two-dimensional radiation image and the tomographic image is performed by performing image analysis by displaying the two-dimensional radiation image on a display device such as a liquid crystal monitor, designating a position where it is considered that a lesion is present on the two-dimensional radiation image through clicking or the like, and displaying the tomographic image obtained by enlarging a region in the vicinity of the lesion. Further, there is also a case where cross reference is performed by simultaneously displaying a two-dimensional radiation image and tomographic images corresponding to an imaging direction of the two-dimensional radiation image. In either case, the tomographic image is automatically or manually displayed while switching tomographic planes.

A plurality of tomographic images are acquired by the tomography imaging such as the above-mentioned tomosynthesis imaging, but since there are a tomographic image of a tomographic plane on which a lesion or the like is included and a tomographic image of a tomographic plane on which the lesion is not included, a user such as a doctor who performs image analysis needs to perform interpretation while switching the plurality of tomographic images. Accordingly, in a case where image diagnosis is performed by performing cross reference between two-dimensional radiation images and tomographic images, its operation is troublesome as compared with a case where only the two-dimensional radiation images are used, and consequently, it takes long time to perform diagnosis.

Accordingly, a technique for creating a depth map in which each position on a two-dimensional radiation image and depth information indicating a depth directional position of a tomographic plane corresponding to each position are associated with each other, and extracting and displaying, in a case where a reference position is designated in the two-dimensional radiation image, a tomographic image corresponding to the depth of the reference position has been proposed (see WO14/203531A).

SUMMARY OF THE INVENTION

However, in a two-dimensional radiation image, since a plurality of structures are displayed in an overlapping manner in a depth direction of a subject, in the technique of WO14/203531A, it is not possible to correctly display a tomographic image on a tomographic plane corresponding to a structure that a user wants to observe in detail. For example, in a case where calcification that overlaps a tumor exists on a two-dimensional radiation image, even though a user sets the tumor as a region-of-interest, there is a tomographic image of a tomographic plane corresponding to the calcification is displayed.

The present disclosure has been made in view of the above circumstances, and an object of the invention is to provide an image display apparatus, a radiation imaging display system, an image display method, and an image display program capable of accurately displaying, in performing image diagnosis by performing cross reference between a two-dimensional radiation image and a tomographic image, a tomographic image corresponding to a designated position on the two-dimensional radiation image.

According to an aspect of the invention, there is provided an image display apparatus comprising: a depth map creating unit that creates, on the basis of a two-dimensional radiation image and a plurality of tomographic images for the same subject, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information.

In the image display apparatus according to the present disclosure, the depth map creating unit may create the plurality of depth maps for each frequency component of the two-dimensional radiation image and the plurality of tomographic images.

In the image display apparatus according to the present disclosure, the depth map creating unit may create the plurality of depth maps for each object in the two-dimensional radiation image and the plurality of tomographic images.

In the image display apparatus according to the present disclosure, the depth map creating unit may create the depth maps by associating each position on the two-dimensional radiation image and the depth information indicating the depth directional position of the tomographic plane corresponding to each position on the basis of a correlation between each position on the two-dimensional radiation image and the plurality of tomographic images.

Further, in the image display apparatus according to the present disclosure, the depth map creating unit may divide the two-dimensional image into a plurality of regions, and may create the depth maps by associating a position of each region on the two-dimensional radiation image and the depth information indicating the depth directional position of the tomographic plane corresponding to the position of each region.

The image display apparatus according to the present disclosure may further comprise a display control unit that specifies depth information on a reference position in the two-dimensional radiation image with reference to the depth maps and displays a tomographic image of a tomographic plane indicated by the specified depth information on a display unit.

Further, the image display apparatus according to the present disclosure may further comprise: an input unit that receives designation of any position on the two-dimensional radiation image displayed on the display unit, in which the display control unit displays the tomographic images on the display unit using the designated position as the reference position.

Further, in the image display apparatus according to the present disclosure, the display control unit may determine the depth map to be referred to from the plurality of depth maps on the basis of an input method in a case where the input unit receives the designation.

In addition, in the image display apparatus according to the present disclosure, the display control unit may determine the depth map to be referred to from the plurality of depth maps on the basis of an object at the designated position on the two-dimensional radiation image.

According to another aspect of the present disclosure, there is provided a radiation imaging display system comprising: an imaging unit that acquires a two-dimensional radiation image and a plurality of tomographic images for the same subject; and the image display apparatus according to the present disclosure.

According to still another aspect of the present disclosure, there is provided an image display method comprising: creating, on the basis of a two-dimensional radiation image and a plurality of tomographic images for the same subject, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information.

According to still another aspect of the present disclosure, there is provided an image display program for causing a computer to execute a procedure of creating, on the basis of a two-dimensional radiation image and a plurality of tomographic images for the same subject, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information.

According to the present disclosure, it is possible to provide an image display apparatus, a radiation imaging display system, an image display method, and an image display program capable of accurately displaying, in performing image diagnosis by performing cross reference between a two-dimensional radiation image and tomographic images, a tomographic image corresponding to a designated position on the two-dimensional radiation image.

BRIEF DESCRIPTION OF THE DRAWINGS

FIG. 6 is a diagram for explaining creation of a depth map.

FIG. 7 is a diagram showing the depth map.

FIG. 9 is a flowchart of an image display process performed in the first embodiment.

FIG. 10 is a diagram showing an example of an image displayed on a monitor.

DESCRIPTION OF THE PREFERRED EMBODIMENTS

Figure 1:
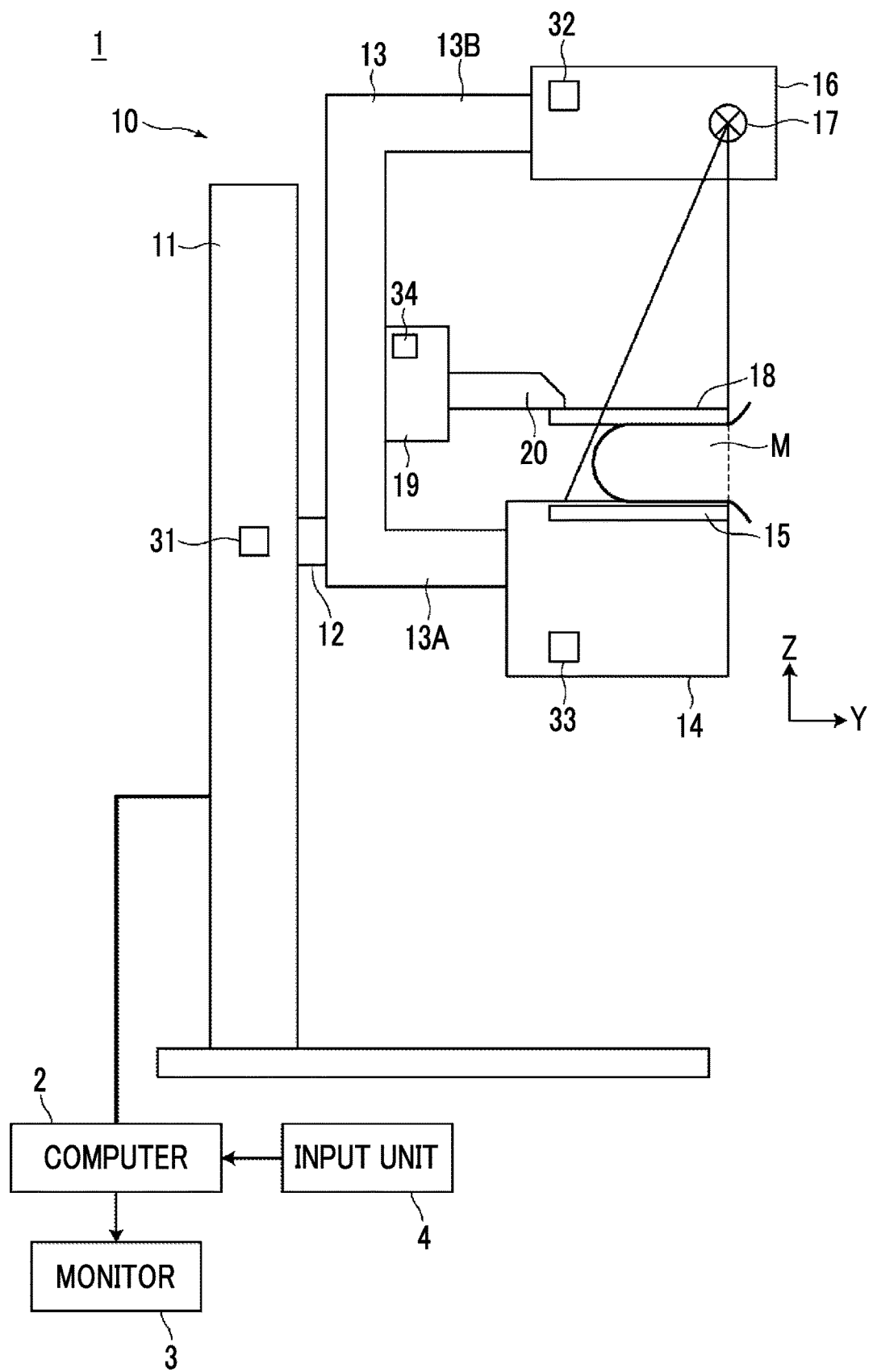
FIG. 1 is a schematic configuration diagram of a radiation imaging display system to which an image display apparatus according to an embodiment of the invention is applied.

Hereinafter, embodiments of the invention will be described with reference to the accompanying drawings. FIG. 1 is a schematic configuration diagram of a radiation imaging display system to which an image display apparatus according to an embodiment of the invention is applied. A radiation imaging display system 1 is a mammography imaging apparatus that obtains a plurality of radiation images by imaging a breast M in different imaging directions to generate a two-dimensional radiation image by performing plain radiography for the breast and performing tomosynthesis imaging for the breast. As shown in FIG. 1, the radiation imaging display system 1 comprises an imaging unit 10, a computer (image display apparatus) 2 connected to the imaging unit 10, a monitor (display unit) 3 connected to the computer 2, and an input unit 4.

Figure 2:
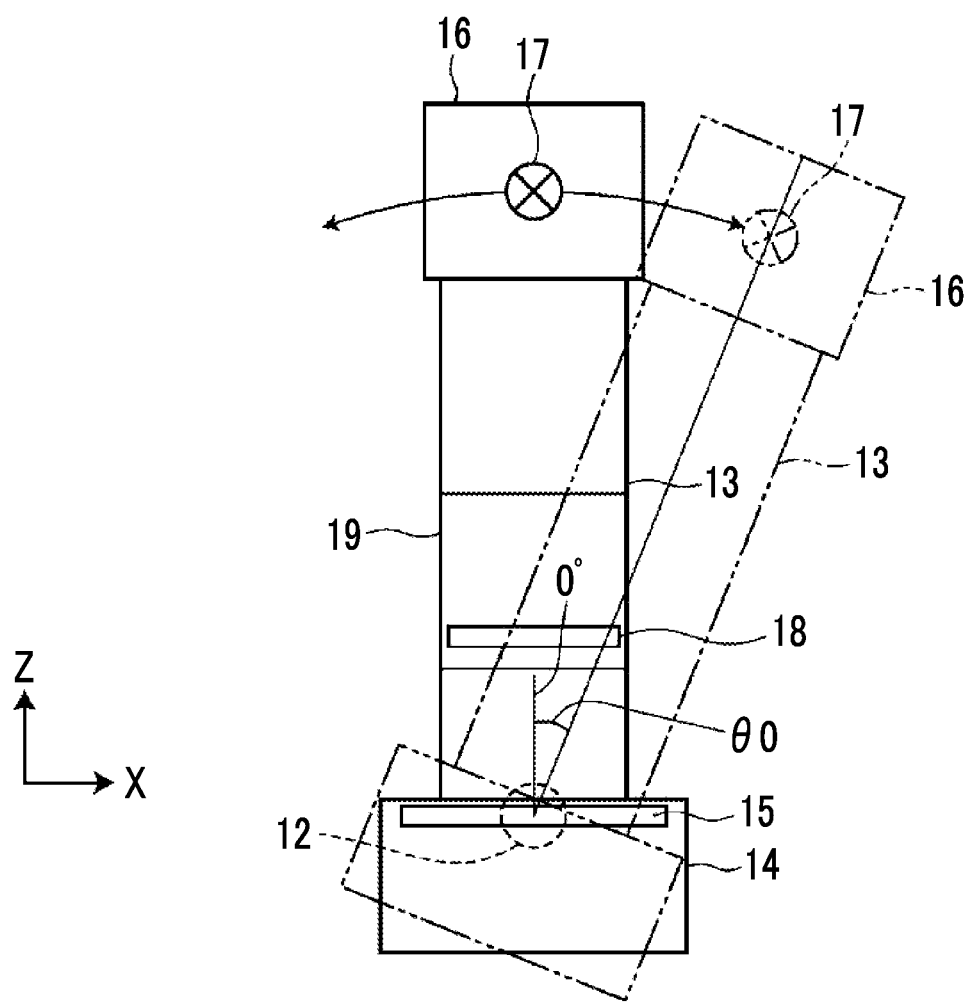
FIG. 2 is a diagram showing an arm unit of the radiation imaging display system shown in FIG. 1, seen in a right direction of FIG. 1.

The imaging unit 10 comprises a base 11, a rotary shaft 12 that is movable in a vertical direction (Z-direction) and is rotatable with respect to the base 11, and an arm unit 13 that is connected to the base 11 through the rotary shaft 12. In FIG. 2, the arm unit 13 viewed in a right direction (Y-direction) in FIG. 1 is shown.

The arm unit 13 is in a shape of "C", and an imaging stand 14 is attached to one end part 13A thereof, and a radiation irradiation unit 16 is attached to the other end part 13B thereof to face the imaging stand 14. The arm unit 13 is configured so that the end part 13A to which the imaging stand 14 is attached and the end part 13B to which the radiation irradiation unit 16 is attached are integrally rotatable and only the end part 13B to which the radiation irradiation unit 16 is attached is rotatable. Thus, the imaging stand 14 and the radiation irradiation unit 16 are integrally rotatable, and only the radiation irradiation unit 16 is rotatable in a state where the imaging stand 14 is fixed. In FIG. 2, in a case where a clockwise rotation of FIG. 2 is positive, a rotational position where the arm unit 13 is parallel to the base 11 is set as a 0 degree, and a state where the arm unit 13 integrally rotates the imaging stand 14 and the radiation irradiation unit 16 clockwise by $\theta 0$ degrees is indicated by a virtual line. The rotation and the vertical movement of the arm unit 13 are controlled by an arm controller 31 that is assembled in the base 11.

Inside the imaging stand 14, a radiation detector 15 such as a flat panel detector, and a detector controller 33 that controls readout of a charge signal from the radiation detector 15 are provided.

Further, inside the imaging stand 14, a circuit board where a charge amplifier that converts the charge signal read out from the radiation detector 15 into a voltage signal, a correlated double sampling circuit that samples the voltage signal output from the charge amplifier, an analog to digital (AD) conversion unit that converts the voltage signal to a digital signal, and the like are provided is also provided, for example.

The radiation detector 15 is able to repeatedly perform recording and readout of a radiation image, which may employ a so-called direct type radiation detector that directly receives irradiation of radiation to generate charges, or may employ a so-called indirect type radiation detector that once converts radiation into visible light and converts the visible light into a charge signal. Further, as a method for reading out the radiation image signal, a so-called TFT (thin film transistor) readout method for reading out the radiation image signal by turning on and off a TFT switch, or a so-called optical readout method for reading out the radiation image signal by irradiating readout light is preferably used, but the present disclosure is not limited thereto, and other methods may be used.

Inside the radiation irradiation unit 16, a radiation source 17 and a radiation source controller 32 are provided. The radiation source controller 32 controls a timing when radiation is emitted from the radiation source 17, and radiation generating conditions in the radiation source 17 (a tube current, a period of time, a tube current time product, and the like).

Further, at a central portion of the arm unit 13, a compression plate 18 that is arranged above the imaging stand 14 to squeeze and press a breast, a support portion 20 that supports the compression plate 18, and a moving mechanism 19 that moves the support portion 20 in the vertical direction (Z-direction) are provided. The position and a compression pressure of the compression plate 18 are controlled by a compression plate controller 34.

Figure 3:
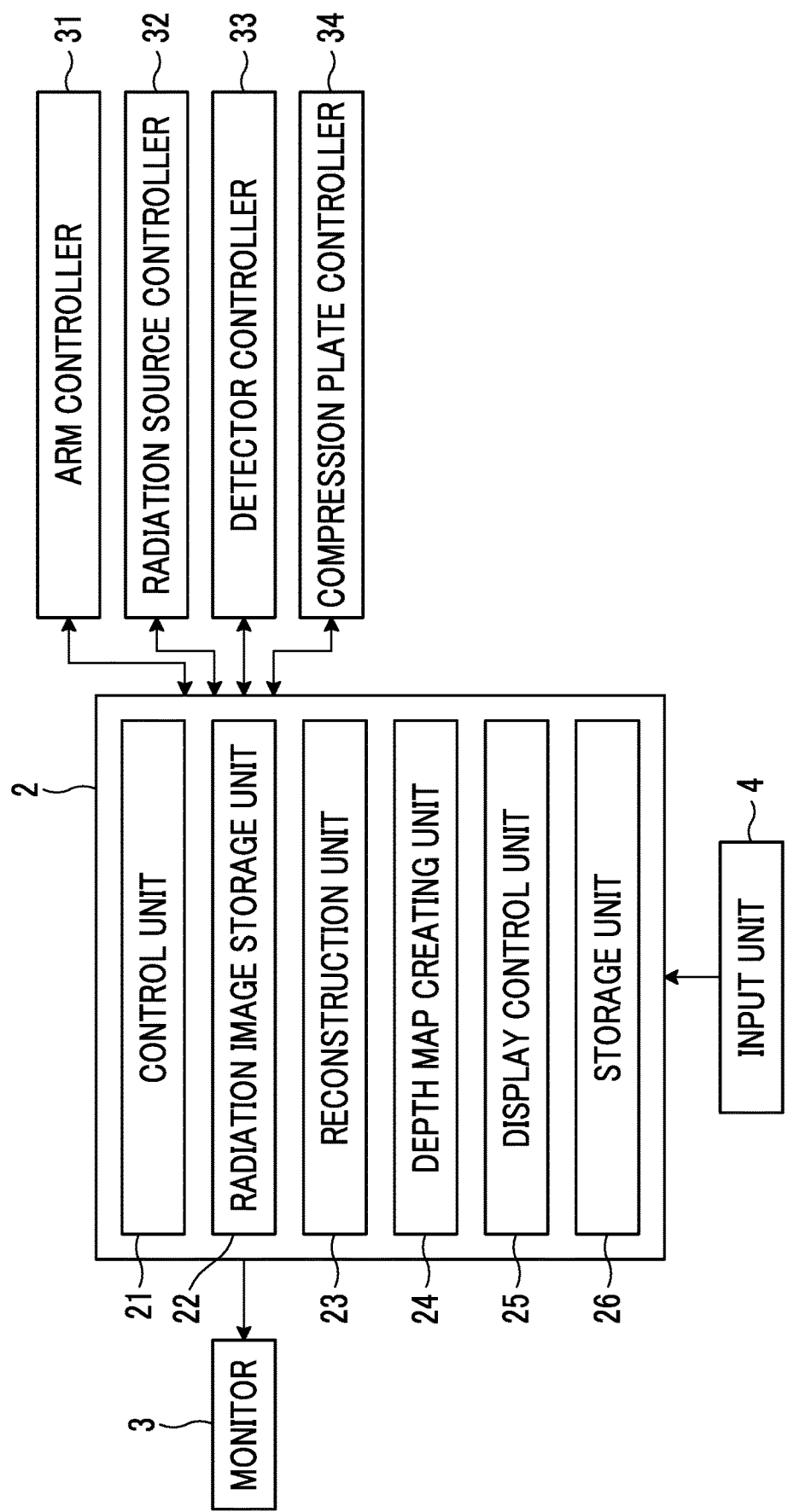
FIG. 3 is a block diagram showing a schematic internal configuration of a computer of the radiation imaging display system shown in FIG. 1.

The computer 2 comprises a central processing unit (CPU), a storage device such as a semiconductor memory, a hard disk or a solid state drive (SSD), and the like, and by such hardware, a control unit 21, a radiation image storage unit 22, a reconstruction unit 23, a depth map creating unit 24, a display control unit 25, a storage unit 26 as shown in FIG. 3 are configured.

The control unit 21 outputs a predetermined control signal to various controllers 31 to 34 to control the entire apparatus.

The radiation image storage unit 22 stores a plurality of radiation images detected by the radiation detector 15 by performing imaging in a predetermined imaging direction while rotating both the end parts 13A and 13B of the arm unit 13. As the imaging direction of the breast M, there are craniocaudal (CC) imaging for performing imaging by irradiating radiation from an upper side, mediolateral (ML) imaging for performing imaging by irradiating radiation from a lateral side, a mediolateral oblique (MLO) imaging for performing imaging by irradiating radiation in an oblique direction, and the arm unit 13 is rotated to be positioned in accordance with these imaging directions to perform imaging. FIG. 1 shows positioning in a case where the craniocaudal (CC) imaging is performed. Further, in this embodiment, it is not necessary to perform all of the CC imaging, the ML imaging, and MLO imaging, and at least one thereof may be performed.

Figure 4:
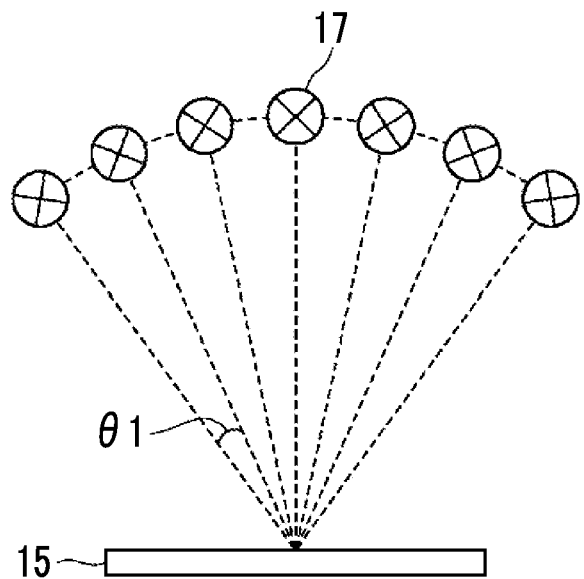
FIG. 4 is a diagram showing a plurality of imaging directions.

In addition, in this embodiment, as shown in FIG. 4, a plurality of radiation images detected by the radiation detector 15 through imaging in a plurality of imaging directions with an interval of a predetermined angle $\theta 1$ by rotating only the end part 13B to which the radiation irradiation unit 16 is attached, that is, through tomosynthesis imaging, are also stored. In this embodiment, in each of the imaging directions, a plurality of radiation images are acquired by performing the tomosynthesis imaging, and tomographic images of the breast M generated from the plurality of radiation images and a two-dimensional radiation image acquired by plain radiography are displayed.

Figure 5:
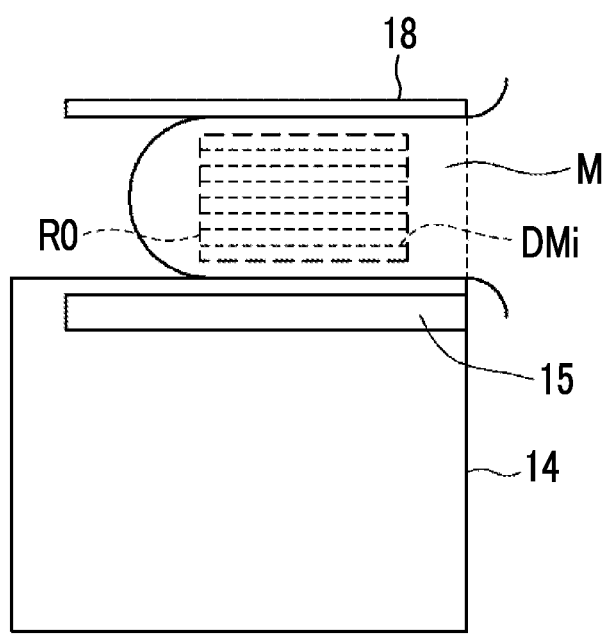
FIG. 5 is a diagram showing a reconstruction range of a tomographic image.

The reconstruction unit 23 reconstructs the plurality of radiation images stored in the radiation image storage unit 22 to generate a tomographic image in which a desired tomographic plane of the breast M is emphasized. Specifically, the reconstruction unit 23 generates a tomographic image by reconstructing these radiation images using back-projection methods such as a simple back-projection method or a filtered back-projection technique. As shown in FIG. 5, the reconstruction unit 23 generates a tomographic image at each of a plurality of tomographic planes DMi (i=1 to n, where n represents the number of tomographic planes) parallel to a detection surface of the radiation detector 15 in a reconstruction range R0 that is predetermined in the breast M.

The depth map creating unit 24 creates a plurality of depth maps in which each position on a two-dimensional radiation image acquired in each of the imaging directions and depth information indicating a depth directional position from a reference position of a tomographic plane corresponding to each position are associated with each other while changing a correspondence relationship between each position on the two-dimensional radiation image and the depth information. FIG. 6 is a diagram for describing creation of a depth map. In this embodiment, as described above, in one imaging direction, a plurality of tomographic images Di (i=1 to n, where n represents the number of tomographic planes) and one two-dimensional radiation image G0 are stored in the radiation image storage unit 22. In this embodiment, for example, an example in which an interval between the tomographic planes is 1 mm and the tomographic images Di are generated on the tomographic planes DMi from a depth of 10 mm to a depth of 40 mm at 1 mm intervals toward the radiation source 17 using the detection surface of the radiation detector 15 as a reference position is shown, but the invention is not limited thereto.

The depth map creating unit 24 divides the two-dimensional radiation image G0 into a plurality of regions, and obtains a correlation between each region obtained by the division and the plurality of tomographic images Di for each frequency component. For example, as shown in FIG. 6, the two-dimensional radiation image G0 is divided into regions of 6×8, and with respect to the divided one region A1, a correlation between the divided one region A1 and the plurality of tomographic images Di is obtained, for each frequency component. Further, depths, from the reference position, of the tomographic planes of the tomographic images Di including a region where the correlation becomes the largest are associated with the position of the region A1 to create a plurality of depth maps.

In this way, by creating the depth map in which each position on the two-dimensional radiation image and the depth information indicating the depth directional position of the tomographic plane corresponding to each position are associated with each other, on the basis of the correlation between each position on the two-dimensional radiation image and the plurality of tomographic images, it is possible to easily associate each position on the two-dimensional radiation image and the depth directional position of the tomographic plane.

FIG. 7 is a diagram showing a depth map. For example, with respect to the 2-dimensional radiation image G0 and the plurality of tomographic images Di, a bandwidth of a frequency component of an image is divided into three portions, and a high-frequency component depth map MP1, a medium-frequency component depth map MP2, and a low-frequency component depth map MP3 are created in order from the highest frequency component.

Specifically, in a high-frequency component image of the two-dimensional radiation image G0, in a case where the depth of a high-frequency component tomographic image including a region where a correlation with a region A1 in FIG. 6 becomes highest is 30 mm, the high-frequency component depth map MP1 associated with 30 mm is created at the position of the region A1. Further, in a medium-frequency component image of the two-dimensional radiation image G0, in a case where the depth of a medium-frequency component tomographic image including the region where the correlation with the region A1 in FIG. 6 becomes highest is 25 mm, the medium-frequency component depth map MP2 associated with 25 mm is created at the position of the region A1. In addition, in a low-frequency component image of the two-dimensional radiation image G0, in a case where the depth of a low-frequency component tomographic image including the region where the correlation with the region A1 in FIG. 6 becomes highest is 20 mm, the low-frequency component depth map MP3 associated with 20 mm is created at the position of the region A1. In the depth maps MP1 to MP3, a predetermined depth (for example, 10 mm) may be associated with a region that does not include the breast M in the two-dimensional radiation image G0. The created depth maps MP1 to MP3 are stored in the storage unit 26.

Lesions detected in the two-dimensional radiation image G0 (for example, calcification, spicule, tumor, and the like) may be divided for each frequency component in accordance with their structures and sizes. For example, a calcification appears as a high-frequency component in the two-dimensional radiation image G0, a spicule appears as a medium-frequency component in the two-dimensional radiation image G0, and a tumor appears as a low-frequency component in the two-dimensional radiation image G0. Accordingly, by creating the plurality of depth maps MP1 to MP3 for each frequency component, even in a case where a plurality of structures (for example, the calcification, the spicule, the tumor, and the like) are displayed in an overlapping manner at the same region of the two-dimensional radiation image G0, it is possible to specify the depth of a desired structure by selecting a corresponding depth map.

The depth maps MP1 to MP3 are created, for each frequency component, by associating a position of each region on the two-dimensional radiation image G0 with depth information indicating a depth directional position of a tomographic plane corresponding to the position of each region, but instead, may be created by associating a position of each pixel on the two-dimensional radiation image with depth information indicating a depth directional position of a tomographic plane corresponding to the position of each pixel. In this case, the depth maps may be created by setting a region of a predetermined size centering around a target pixel on the two-dimensional radiation image, obtaining a correlation between the region and the tomographic images Di, and associating the depth, from the reference position, of a tomographic plane of a tomographic image Di including a region where the correlation becomes the largest with the position of the target pixel for which the region is set.

On the other hand, at the time of acquisition of the two-dimensional radiation image G0 and reconstruction of the plurality of tomographic images Di, a positional relationship between the radiation source 17 and the radiation detector 15 is known in advance. Thus, on the basis of the positional relationship between the radiation source 17 and the radiation detector 15, depth maps MP may be generated by associating the position of each pixel on the two-dimensional radiation image G0 with the depth information indicating the depth directional position of the tomographic plane corresponding to the position of each pixel. In this case, from a certain pixel position on the two-dimensional radiation image G0, and the positional relationship between the radiation source 17 and the radiation detector 15, a projection ray of radiation passing through the pixel position may be specified. If the projection ray can be specified, a position on a tomographic image Di through which the projection ray passes may be specified. Further, the plurality of depth maps MP1 to MP3 may be created for each frequency component by associating a depth directional position of a tomographic plane of a tomographic image having a maximum pixel value, for example, among the plurality of tomographic images Di on the projection ray, with the pixel position where the projection ray passes.

Further, in the above description, the two-dimensional radiation image G0 is divided into regions of 6×8, but for example, divided regions divided into 10 pixels×10 pixels, 1 cm×1 cm, or the like may be a predetermined size. In addition, in the above description, with respect to the two-dimensional radiation image G0 and the plurality of tomographic images Di, the bandwidth of the frequency component of the image is divided into three portions to create three types of depth maps MP1 to MP3, but instead, two, four or more types of depth maps may be created.

Further, a known region extraction process may be performed with respect to the two-dimensional radiation image G0, and a plurality of depth maps may be created for each object in the image. Specifically, a plurality of depth maps may be created for each lesion of the breast M (for example, calcification, spicule, tumor, and the like). In this case, the depth of each region in the depth maps may be obtained for each pixel included in each region, and an average value or a mode of the obtained depths in each region may be set to the depth of the region to create the depth maps. In the case of such an embodiment, similar to the case where the plurality of depth maps MP1 to MP3 are created for each frequency component, even in a case where the plurality of structures (for example, calcification, spicule, tumor, and the like) are displayed in an overlapping manner at the same region of the two-dimensional radiation image G0, it is possible to specify the depth of a desired structure by selecting a corresponding depth map.

The display control unit 25 displays a two-dimensional radiation image in a designated imaging direction on the monitor 3 in accordance with an instruction from the input unit 4. Further, the display control unit 25 displays tomographic images on the monitor 3 with reference to any one of the depth maps MP1 to MP3 in accordance with an instruction from the input unit 4. The display of the tomographic images will be described later.

The monitor 3 is configured of a known display device such as a cathode ray tube (CRT), or a liquid crystal display, and displays the two-dimensional radiation image G0 and the tomographic images Di output from the computer 2.

The input unit 4 is configured of a pointing device such as a keyboard or a mouse, for example, and receives input of imaging conditions, input of an imaging start instruction, or the like, from an operator.

Figure 8:
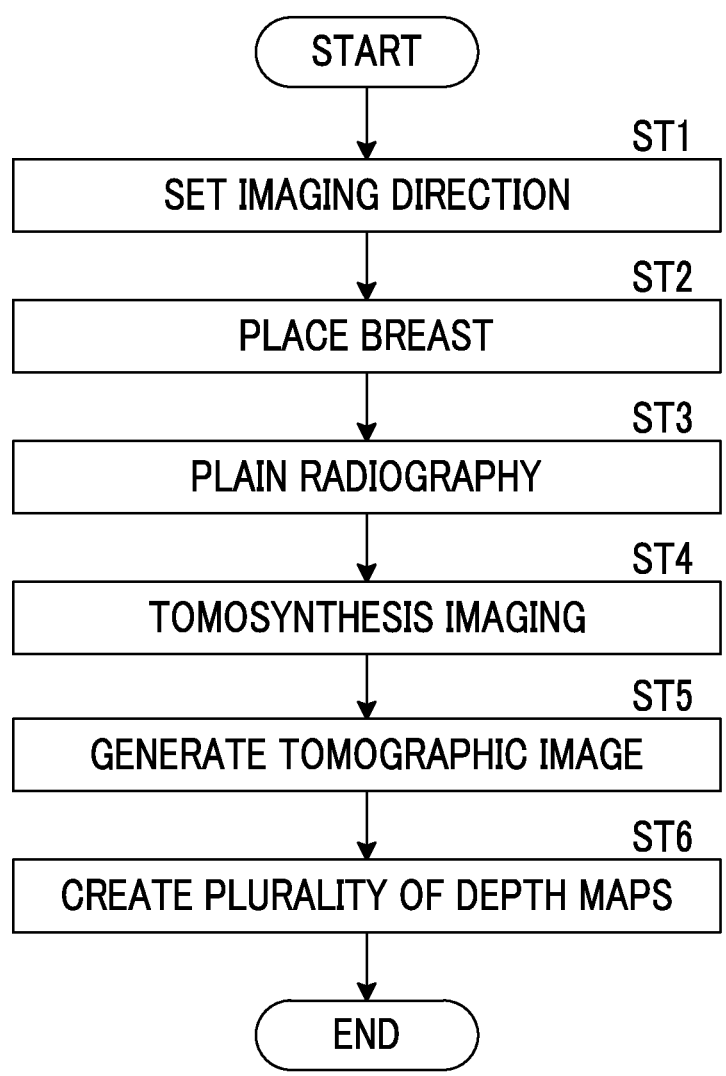
FIG. 8 is a flowchart showing processes performed in a first embodiment.

Then, processes performed in this embodiment will be described. FIG. 8 is a flowchart illustrating an imaging process performed in a first embodiment. First, an imaging direction is set in accordance with an instruction from the input unit 4 (step ST1). Specifically, first, the control unit 21 outputs information on the imaging direction instructed from the input unit 4 to the arm controller 31. The arm controller 31 outputs a control signal so that the position of the arm unit 13 becomes a position corresponding to the imaging direction designated with respect to the base 11. Then, in accordance with the control signal output from the arm controller 31, the arm unit 13 causes the imaging stand 14 and the radiation irradiation unit 16 to be integrally rotated. The arm controller 31 stops the arm unit 13 in a state where the arm unit 13 is at a position corresponding to the designated imaging direction. In this way, the imaging direction is set. Then, the breast M of a patient is placed on the imaging stand 14, and the breast M is compressed by the compression plate 18 under a predetermined pressure (step ST2). After various imaging conditions are input through the input unit 4, an imaging start instruction is input.

In a case where the imaging start instruction is input through the input unit 4, plain radiography is performed to acquire the two-dimensional radiation image G0 (step ST3). Specifically, in accordance with the imaging start instruction, the control unit 21 outputs a control signal for irradiation of radiation and readout of a radiation image signal to the radiation source controller 32 and the detector controller 33. In accordance with the control signal, radiation is emitted from the radiation source 17, a radiation image obtained by imaging the breast M is detected by the radiation detector 15, a radiation image signal is read out through the radiation detector 15 by the detector controller 33, predetermined signal processing is performed for the radiation image signal, and then, the result is stored in the radiation image storage unit 22 of the computer 2 as the two-dimensional radiation image G0.

Then, tomosynthesis imaging is performed (step ST4). The tomosynthesis imaging is performed by irradiating the breast M with radiation while rotating the radiation irradiation unit 16 with respect to the imaging stand 14 using the arm unit 13 in a state where the imaging stand 14 is fixed. Specifically, first, the control unit 21 reads out an angle θ1 for defining a predetermined imaging interval, and outputs information on the read out angle θ1 to the arm controller 31.

Further, the arm controller 31 receives the information on the angle θ1 output from the control unit 21, and the arm controller 31 first outputs a control signal so that the position of the end part of the arm unit 13 to which the radiation irradiation unit 16 is attached is at an initial position of being most inclined with respect to the imaging stand 14.

Then, in a state where the arm unit 13 is at the initial position in accordance with the control signal output from the arm controller 31, the control unit 21 outputs a control signal for irradiation of radiation and readout of a radiation image signal to the radiation source controller 32 and the detector controller 33. In accordance with the control signal, radiation is emitted from the radiation source 17, a radiation image obtained by imaging the breast M at the initial position is detected by the radiation detector 15, a radiation image signal is read out through the radiation detector 15 by the detector controller 33, predetermined signal processing is performed for the radiation image signal, and then, the result is stored in the radiation image storage unit 22 of the computer 2 as a radiation image for creating a tomographic image.

Then, the arm controller 31 outputs a control signal to rotate the arm unit 13 by the degree of θ1 from the initial position. That is, in this embodiment, the arm controller 31 outputs the control signal to rotate the arm unit 13 by the degree of θ1 from the initial position toward an end position where final imaging is performed. In a state where the arm unit 13 is rotated by the degree of θ1 in accordance with the control signal output from the arm controller 31, the control unit 21 outputs a control signal for irradiation of radiation and readout of a radiation image signal to the radiation source controller 32 and the detector controller 33.

Specifically, the control unit 21 outputs a control signal for irradiation of radiation and readout of a radiation image signal to the radiation source controller 32 and the detector controller 33. In accordance with the control signal, radiation is emitted from the radiation source 17, a radiation image obtained by imaging the breast M at a position that is moved from the position initial by the degree of θ1 is detected by the radiation detector 15, a radiation image signal is read out by the detector controller 33, predetermined signal processing is performed, and then, the result is stored in the radiation image storage unit 22 of the computer 2 as a radiation image.

Further, the process is repeatedly performed until the arm unit 13 is rotated to the end position, and thus, a plurality of radiation images are stored in the radiation image storage unit 22.

Then, the reconstruction unit 23 reconstructs the plurality of radiation images in a reconstruction range of tomographic images of the breast M to generate the plurality of tomographic images Di (step ST5). The plurality of tomographic images Di are stored in the radiation image storage unit 22. The imaging process is repeatedly performed until the two-dimensional radiation image G0 and the tomographic images Di are generated, in all imaging directions that are determined in advance with respect to each of the left and right breasts M.

Then, the depth map creating unit 24 creates the plurality of depth maps MP1 to MP3 (step ST6) in which each position on the two-dimensional radiation image G0 acquired with respect to each of the imaging directions and depth information indicating a depth directional position of a tomographic plane corresponding to each position are associated with each other, for each frequency component, and then, the process is terminated. The created depth maps MP1 to MP3 are stored in the storage unit 26.

FIG. 9 is a flowchart of an image display process performed in this embodiment. In a case where an imaging direction instruction and an image display instruction are input through the input unit 4, the display control unit 25 reads out the two-dimensional radiation image G0 in the designated imaging direction from the radiation image storage unit 22, and displays the result on the monitor 3 (step ST11).

Then, the input unit 4 receives designation of a position in the two-dimensional radiation image G0 and the type of a depth map (step ST12). The designation of the depth map in the input unit 4 may be performed by receiving designation of the depth map on the basis of an input method at the time of the designation of the position. For example, in a case where a mouse is used as the input unit 4, the high-frequency component depth map MP1 may be designated in a case where the position is designated through a left click, the medium-frequency component depth map MP2 may be designated in a case where the position is designated through a wheel click, and the low-frequency component depth map MP3 may be designated in a case where the position is designated through a right click.

Instead of the above designation method, in a case where depth maps are created for each lesion of the breast M, a calcification depth map MP1 may be designated in a case where the position is designated through a left click, a spicule depth map MP2 may be designated in a case where the position is designated through a wheel click, and a tumor depth map MP3 may be designated in a case where the position is designated through a right click. Further, with respect to an input method through the mouse, the designation of the type of the depth map may be received in accordance with a right click, a left click, or a left and right simultaneous click, or may be received in accordance with the number of left clicks (for example, 1 click, 2 clicks, 3 clicks, or the like). Further, a user may receive the designation of the type of the depth map on the basis of a structure (object) of a region designated on the two-dimensional radiation image G0.

The display control unit 25 acquires depth information corresponding to the position designated on the two-dimensional radiation image G0 with reference to the selected depth map (step ST13), and displays the tomographic image Di on a tomographic plane corresponding to the acquired depth information on the monitor 3 (step ST14), and then, the process is terminated.

FIG. 10 is a diagram showing an image displayed on the monitor 3. As shown in FIG. 10, the two-dimensional radiation image G0 is displayed in a left region of a screen of the monitor 3, and the tomographic images Di corresponding to the position P0 designated on the two-dimensional radiation image G0 are displayed in the vicinity of the two-dimensional radiation image G0, specifically, in a right region of the two-dimensional radiation image G0. For example, in a case where the high-frequency component depth map MP1 is designated from the plurality of depth maps MP1 to MP3 and the position designated in the two-dimensional radiation image G0 corresponds to a region surrounded by a thick line of the high-frequency component depth map MP1 shown in FIG. 7, since the depth from the reference position is 30 mm, a tomographic image on a tomographic plane corresponding to the depth of 30 mm is displayed on the monitor 3. Here, tomographic planes to be displayed may be sequentially switched in accordance with an instruction through the input unit 4, and the tomographic images may be displayed as a motion picture in which the tomographic planes are sequentially switched. In the displayed tomographic image Di, a scale 40 indicating a depth directional position of a tomographic plane that is being displayed in all tomographic planes and a numerical value 41 indicating the depth of the tomographic plane are displayed in parallel.

Figure 11:
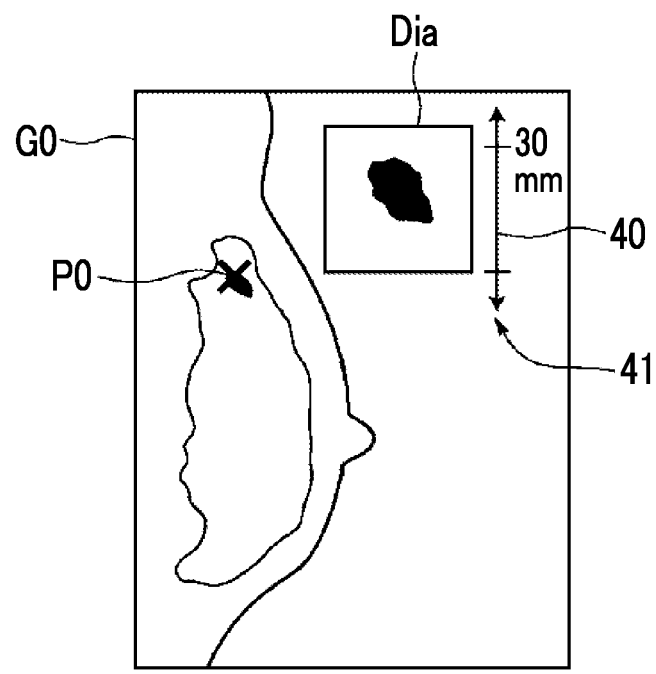
FIG. 11 is a diagram showing an example of an image displayed on the monitor.

As shown in FIG. 11, a region of a predetermined range including the position designated in the two-dimensional radiation image G0 may be cut out from the corresponding tomographic image Di, and a cut-out tomographic image Dia may be displayed on the two-dimensional radiation image G0 in an overlapping manner. In this case, the tomographic image Dia may be displayed as a motion picture, or may be displayed together with the scale 40 indicating the depth directional position on the tomographic plane and the numerical value 41 indicating the depth of the tomographic plane.

Figure 12:
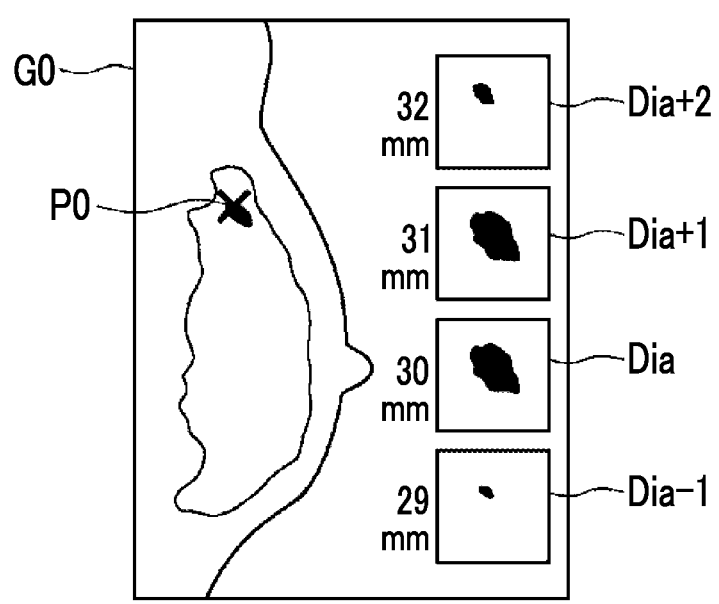
FIG. 12 is a diagram showing an example of an image displayed on the monitor.

Further, as shown in FIG. 12, the region of the predetermined range including the position designated in the two-dimensional radiation image G0 may be cut out from the corresponding tomographic image Di, regions corresponding to the cut-out region with respect to tomographic images of a plurality of tomographic planes that are before and behind adjacent to the tomographic plane corresponding to the designated position may be cut out, and tomographic images Dia+2, Dia+1, Dia, and Dia−1 of the plurality of cut-out tomographic planes may be displayed in parallel. In this case, numerical values indicating the depths of the plurality of tomographic planes may be displayed together. Further, in this case, an interval of tomographic planes to be displayed, as well as the adjacent tomographic planes, may be a set as a predetermined interval (for example, 5 mm).

As described above, in this embodiment, a plurality of depth maps in which each position on the two-dimensional radiation image G0 and depth information indicating a depth directional position of a tomographic plane corresponding to each position are associated with each other are created while changing a correspondence relationship between each position on the two-dimensional radiation image and the depth information, on the basis of the two-dimensional radiation image G0 and the plurality of tomographic images Di of the same object. Accordingly, in performing image diagnosis by performing cross reference between the two-dimensional radiation image G0 and the tomographic images Di, it is possible to easily designate the position of a lesion by first referring to the two-dimensional radiation image G0. Further, by referring to any one of the plurality of depth maps MP1 to MP3 corresponding to the type of a lesion, it is possible to rapidly specify the tomographic images Di of tomographic planes corresponding to the position of a designated lesion. Accordingly, it is possible to rapidly display the specified tomographic images Di together with the two-dimensional radiation image G0. From the above description, even in a case where a plurality of structures (for example, calcification, spicule, tumor, and the like) are displayed in an overlapping manner at the same region of the two-dimensional radiation image G0, it is possible to perform image diagnosis with high efficiency by performing cross reference between the two-dimensional radiation image G0 and the tomographic images Di.

Further, by dividing the two-dimensional radiation image G0 into a plurality of regions and creating the depth maps MP in which a position of each region on the two-dimensional radiation image G0 and depth information corresponding to the position of each region are associated with each other, even in a case where an operator designates as a rough position in designating a region-of-interest, it is possible to stably display a tomographic image of a desired tomographic plane.

In this embodiment, depth maps MP are created in association with all regions of the two-dimensional radiation image G0, but for example, a region where the breast M in the two-dimensional radiation image G0 is included may be extracted, and the plurality of depth maps MP1 to MP3 may be created only with respect to the region where the breast M is included. As described above, by creating the depth maps MP1 to MP3 only with respect to the region where the breast M is included, it is possible to shorten a calculation time for creating the depth maps MP1 to MP3. In this case, in a case where a position of an object other than the breast M is indicated in the displayed two-dimensional radiation image G0, a warning may be given that there is no corresponding tomographic image at the position, or a tomographic image corresponding to a central tomographic plane among the plurality of tomographic images Di may be displayed.

Further, in this embodiment, an image obtained by plain radiography is used as the two-dimensional radiation image G0, but instead, a composite two-dimensional radiation image obtained by combining the plurality of tomographic images Di may be used. As a method for generating the composite two-dimensional radiation image, for example, a method for generating a maximum intensity projection (MIP) image as the composite two-dimensional radiation image from the plurality of tomographic images Di using a maximum intensity projection (MIP) method may be used. For example, in a case where it is determined that a precise examination is necessary as a result of diagnosis using the two-dimensional radiation image G0 acquired through plain radiography in a health checkup and tomographic images are acquired through tomosynthesis imaging in the precise examination, an imaging time of the plain radiography and an imaging time of the tomosynthesis imaging become different from each other. As a result, for example, the degree of compression of the breast M varies, or an imaging position slightly varies, and thus, there is a concern that geometric shapes of the breast M included in the two-dimensional radiation image G0 and the breast M included in the tomographic images Di become different from each other. In such a case, since the positional relationship between the two-dimensional radiation image G0 acquired through the plain radiography and the depth maps MP1 to MP3 varies, there is a concern that each position on the two-dimensional radiation image G0 and the depth information corresponding to each position may not be associated with each other. Accordingly, by creating the depth maps MP1 to MP3 using the composite two-dimensional radiation image obtained by combining the plurality of tomographic images Di as the two-dimensional radiation image G0, it is possible to reliably perform association between each position on the two-dimensional radiation image G0 and the tomographic plane.

Further, in the above-described embodiment, a plurality of radiation images acquired by tomosynthesis imaging are reconstructed to generate tomographic images, but instead, tomographic images may be generated by performing CT imaging in which a radiation source and a radiation detector are disposed to face each other with a subject being placed at the center, the set of the radiation source and the radiation detector is turned around the subject, radiation is irradiated at various angles to capture a plurality of radiation images, and tomographic images are reconstructed using the radiation images at the respective angles to display an unspecified cross section.

Further, in the above-described embodiment, the radiation imaging display system to which the image display apparatus of the invention is applied is used as an apparatus that captures a radiation image of a breast, but in this case, a subject is not limited to the breast, and for example, a radiation imaging display system for imaging a chest portion, a head portion, or the like may be used. Furthermore, appropriate modifications may be made without departing from the concept of the invention.

EXPLANATION OF REFERENCES

1: radiation imaging display system
2: computer
3: monitor
4: input unit
10: imaging unit
11: base
12: rotary shaft
13: arm unit
13A: end part
13B: end part
14: imaging stand
15: radiation detector
16: radiation irradiation unit
17: radiation source
18: compression plate
19: moving mechanism
20: support
21: control unit
22: radiation image storage unit
23: reconstruction unit
24: depth map creating unit
25: display control unit
26: storage unit
31: arm controller
32: radiation source controller
33: detector controller
34: compression plate controller
40: scale
41: numerical value
DMi: tomographic plane
Di: tomographic image
Dia: tomographic image
G0: two-dimensional radiation image
M: breast
MP1: high-frequency component depth map
MP2: medium-frequency component depth map
MP3: low-frequency component depth map

What is claimed is:
1. A depth map creation apparatus comprising:
a processor configured to
acquire a two-dimensional radiation image and a plurality of tomographic images for the same subject; and create, on the basis of a plurality of spatial frequency components of the two-dimensional radiation image and the plurality of tomographic images, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information, each of the plurality of spatial frequency components having a different bandwidth from each other.

2. The depth map creation apparatus according to claim 1, wherein the processor creates the plurality of depth maps for each object in the two-dimensional radiation image and the plurality of tomographic images.

3. The depth map creation apparatus according to claim 1, wherein the processor creates the depth maps by associating each position on the two-dimensional radiation image and the depth information indicating the depth directional position of the tomographic plane corresponding to each position on the basis of a correlation between each position on the two-dimensional radiation image and the plurality of tomographic images.

4. The depth map creation apparatus according to claim 1, wherein the processor divides the two-dimensional image into a plurality of regions, and creates the depth maps by associating a position of each region on the two-dimensional radiation image and the depth information indicating the depth directional position of the tomographic plane corresponding to the position of each region.

5. An image display apparatus comprising:
a processor configured to
acquire a two-dimensional radiation image and a plurality of tomographic images for the same subject and a plurality of depth maps of a plurality of spatial frequency components, in which each position on the two-dimensional radiation image and depth information indicating a depth directional position of a tomographic plane corresponding to each position are associated with each other while changing a correspondence relationship between each position on the two-dimensional radiation image and the depth information, each of the plurality of spatial frequency components having a different bandwidth from each other;
specify depth information on a reference position in the two-dimensional radiation image with reference to the depth maps; and
display a tomographic image of a tomographic plane indicated by the specified depth information on a display.

6. The image display apparatus according to claim 5, the processor further configured to:
receive designation of any position on the two-dimensional radiation image displayed on the display,
wherein the display displays the tomographic images on the display using the designated position as the reference position.

7. The image display apparatus according to claim 6, wherein the processor determines the depth map to be referred to from the plurality of depth maps on the basis of an input method in a case where the designation is received.

8. The image display apparatus according to claim 6, wherein the processor determines the depth map to be referred to from the plurality of depth maps on the basis of an object at the designated position on the two-dimensional radiation image.

9. An image processing system comprising:
a processor configured to
acquire a two-dimensional radiation image and a plurality of tomographic images for the same subject;
create, on the basis of a plurality of spatial frequency components of the two-dimensional radiation image and the plurality of tomographic images, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information, each of the plurality of spatial frequency components having a different bandwidth from each other,
specify depth information on a reference position in the two-dimensional radiation image with reference to the depth maps; and
display a tomographic image of a tomographic plane indicated by the specified depth information on a display.

10. A depth map creation method comprising:
providing a processor configured to
acquire a two-dimensional radiation image and a plurality of tomographic images for the same subject; and
create, on the basis of a plurality of spatial frequency components of the two-dimensional radiation image and the plurality of tomographic images, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information, each of the plurality of spatial frequency components having a different bandwidth from each other.

11. A non-transitory computer-readable storage medium storing an depth map creation program for causing a computer to execute a procedure of creating, on the basis of a plurality of spatial frequency components of a two-dimensional radiation image and a plurality of tomographic images, a plurality of depth maps in which each position on the two-dimensional radiation image and depth information indicating a depth directional position of a tomographic plane corresponding to each position are associated with each other while changing a correspondence relationship between each position on the two-dimensional radiation image and the depth information, each of the plurality of spatial frequency components having a different bandwidth from each other.

* * * * *